(12) United States Patent
Li et al.

(10) Patent No.: US 11,445,959 B2
(45) Date of Patent: Sep. 20, 2022

(54) METHOD AND APPARATUS OF MODULATING A NEURONAL FIRING FREQUENCY AT A BRAIN FUNCTIONAL SITE IN A BRAIN

(71) Applicants: Xiaoping Li, Fukuoka (JP); Qian Xia, Fukuoka (JP); Jessica Li, Fukuoka (JP); Joanna Le Xi Li, Fukuoka (JP)

(72) Inventors: Xiaoping Li, Fukuoka (JP); Qian Xia, Fukuoka (JP); Jessica Li, Fukuoka (JP); Joanna Le Xi Li, Fukuoka (JP)

(*) Notice: Subject to any disclaimer, the term of this patent is extended or adjusted under 35 U.S.C. 154(b) by 693 days.

(21) Appl. No.: 16/113,166

(22) Filed: Aug. 27, 2018

(65) Prior Publication Data
US 2019/0060658 A1    Feb. 28, 2019

Related U.S. Application Data

(60) Provisional application No. 62/550,596, filed on Aug. 26, 2017, provisional application No. 62/578,463, filed on Oct. 29, 2017.

(51) Int. Cl.
| | |
|---|---|
| A61M 21/02 | (2006.01) |
| A61N 2/00 | (2006.01) |
| A61B 5/245 | (2021.01) |
| A61B 5/00 | (2006.01) |
| A61B 5/0507 | (2021.01) |
| A61N 2/02 | (2006.01) |
| A61M 21/00 | (2006.01) |

(52) U.S. Cl.
CPC ............ A61B 5/245 (2021.01); A61B 5/0507 (2013.01); A61B 5/4064 (2013.01);
(Continued)

(58) Field of Classification Search
CPC . A61B 5/04008; A61B 5/4824; A61B 5/4064; A61B 5/0507; A61B 2560/0223;
(Continued)

(56) References Cited

U.S. PATENT DOCUMENTS

| | | | | |
|---|---|---|---|---|
| 4,998,112 A | * | 3/1991 | Franchi | G01R 29/10 343/703 |
| 5,480,374 A | * | 1/1996 | Van Dick | A61N 1/16 600/14 |

(Continued)

FOREIGN PATENT DOCUMENTS

CN    106310526 A  *  1/2017

OTHER PUBLICATIONS

Scammell et al. "Neural Circuitry of Wakefulness and Sleep", Neuron 93, p. 747-765 (Year: 2017).*

(Continued)

*Primary Examiner* — Kaylee R Wilson
(74) *Attorney, Agent, or Firm* — Nixon & Vanderhye P.C.

(57) ABSTRACT

The present application provides a method and an apparatus of modulating a neuronal firing frequency at a brain functional site in a brain, the method comprising: generating an electromagnetic field with its power in variation at the preset modulating frequency; and arranging the generated electromagnetic field near the brain such that the brain functional site is within the range of the near field of the electromagnetic field, to polarize extracellular fluid at the brain functional site with the power of the electromagnetic field, such that a polarization density of the extracellular fluid varies at the preset modulating frequency and neurons in the extracellular fluid are modulated to fire at the preset modulating frequency.

9 Claims, 3 Drawing Sheets

(52) U.S. Cl.
CPC ............ *A61B 5/4824* (2013.01); *A61M 21/02* (2013.01); *A61N 2/006* (2013.01); *A61N 2/02* (2013.01); *A61B 2560/0223* (2013.01); *A61B 2562/0223* (2013.01); *A61M 2021/0055* (2013.01); *A61M 2021/0083* (2013.01); *A61M 2205/3317* (2013.01)

(58) Field of Classification Search
CPC ........ A61B 2562/0223; A61B 5/04001; A61N 2/02; A61N 2/006; A61M 21/02; A61M 2205/3317; A61M 2021/0083; A61M 2021/0055
See application file for complete search history.

(56) References Cited

U.S. PATENT DOCUMENTS

| | | | | |
|---|---|---|---|---|
| 6,828,937 | B1* | 12/2004 | Hilgeman | G01S 5/0221 342/465 |
| 2006/0161225 | A1* | 7/2006 | Sormann | A61N 1/3787 607/61 |
| 2007/0003781 | A1* | 1/2007 | de Rochemont | H01L 23/642 428/615 |
| 2008/0081941 | A1* | 4/2008 | Tononi | A61M 21/02 600/14 |
| 2008/0269851 | A1* | 10/2008 | Deem | A61N 5/02 607/101 |
| 2012/0109241 | A1* | 5/2012 | Rauscher | A61B 5/40 607/9 |
| 2015/0283395 | A1* | 10/2015 | Sabouni | A61N 2/02 600/14 |
| 2016/0278687 | A1* | 9/2016 | Xia | A61B 5/0507 |
| 2017/0028166 | A1* | 2/2017 | Walpole | A61N 2/004 |
| 2018/0256913 | A1* | 9/2018 | Casanova | A61N 2/006 |

OTHER PUBLICATIONS

Xie et al. "Sleep Drives Metabolite Clearance from the Adult Brain", Science. 342 (6156) (Year: 2013).*

* cited by examiner generating an electromagnetic field with its power in variation at the preset modulating frequency — S101 arranging the generated electromagnetic field near the brain such that the targeted brain functional site is within the range of the near field of the electromagnetic field, to polarize extracellular fluid at the brain functional site with the power of the electromagnetic field, such that a polarization density of the extracellular fluid varies at the preset modulating frequency and neurons in the extracellular fluid are modulated to fire at the preset modulating frequency — S102

METHOD AND APPARATUS OF MODULATING A NEURONAL FIRING FREQUENCY AT A BRAIN FUNCTIONAL SITE IN A BRAIN

RELATED APPLICATIONS

This application claims the benefit of priority under 35 USC § 119(e) of U.S. Provisional Patent Application No. 62/550,596 filed 26 Aug. 2017 and U.S. Provisional Patent Application No. 62/578,463 filed 29 Oct. 2017, the contents of which is incorporated herein by reference in their entirety.

TECHNICAL FIELD

The present application relates to a method and an apparatus of modulating brain activities with electromagnetic field, particularly to a method and an apparatus of modulating a neuronal firing frequency at a brain functional site in a brain, in which an electromagnetic field is generated to modulate the neuronal firing frequency of brain functional sites to modulate the activities in the brain.

BACKGROUND

The brain is formed by neurons clustered into multiple brain functional sites. Each of the brain functional sites performs a particular function in the brain, and the function is characteristically related to the neuronal firing frequency at the brain functional site, showing as an activity in the brain. Thus, modulating the neuronal firing frequency at the brain functional site correspondingly modulate the activities in the brain. At each of the brain functional site, the neurons are surrounded by extracellular fluid that contains charged particles, such as calcium, potassium, and chloride. Each of the neurons has gates on its semipermeable membrane, through which the charged particles flow in or out of the neuron. As the charged particles flow (e.g. by diffusion) into and accumulate in the semipermeable membrane of the neuron and build up the membrane potential (i.e. polarization of the neuron) to a threshold value and the membrane receives a stimulation, the gates on the membrane open for all the charged particles to rush flow out of the membrane (causing depolarization of the neuron), forming a cycle of the polarization and depolarization of the neuron. At the end of the depolarization, another cycle of polarization of the neuron starts towards the next depolarization, . . . and so on, forming the firing cycles of the neuron at a firing frequency determining the function state of the brain functional site.

The charged particles flowing by diffusion into the semipermeable membrane of the neuron to build up the membrane potential (i.e. polarization of the neuron) of the neuron depends on the concentration distribution of the charged particles in the surrounding extracellular fluid and therefore can be positively or negatively facilitated by varying the polarization density of the extracellular fluid. By varying the polarization density of the extracellular fluid, the diffusion rate can be varied and then the time taken for the polarization and depolarization of the neuron can be varied. Therefore, changing the variation frequency of the polarization density of the extracellular fluid changes the frequency of the polarization and depolarization cycle of the neuron, i.e. changes the firing rate of the neuron.

SUMMARY

In an aspect, there is provided a method of modulating a neuronal firing frequency at a brain functional site in a brain, comprising:

generating an electromagnetic field with its power in variation at the preset modulating frequency; and arranging the generated electromagnetic field near the brain such that the targeted brain functional site is within the range of the near field of the electromagnetic field, to polarize extracellular fluid at the brain functional site with the power of the electromagnetic field, such that a polarization density of the extracellular fluid varies at the preset modulating frequency and neurons in the extracellular fluid are modulated to fire at the preset modulating frequency.

The near field of the electromagnetic field may be generated by an antenna and satisfy the condition of $$0 < d \leq 0.62 * \sqrt{\frac{D^3}{\lambda}},$$

wherein d represents the distance from the antenna to an edge of the near field where the near field ends, D represents the largest dimension of the antenna, and $\lambda$ represents the wavelength of the generated electromagnetic field in vacuum. Here, given that d satisfies the above condition, the electrical power from the antenna can be effectively transferred onto the targeted brain functional site within the near field through the inductive and capacitive effect of the current and charges in the antenna applied on the targeted brain functional site via the neuronal clusters formed by groups of neurons in the brain, which act as the secondary antennas for receiving the electrical power from the antenna to the targeted brain functional site within the near field.

The wavelength $\lambda$ of the generated electromagnetic field in vacuum is such that the wavelength of the generated electromagnetic field at the brain functional site matches the dimension of the brain functional site. In this way, the brain functional site can be efficiently modulated by the electromagnetic field.

Additionally or alternatively, the wavelength $\lambda$ of the generated electromagnetic field in vacuum may be such that the wavelength of the electromagnetic field at the brain functional site is from 70% to 130% of the dimension of the brain functional site.

The preset modulating frequency is determined based on the operational (or normal) neuronal firing frequency at the brain functional site and is preferably in the range of 1 Hz to 2500 Hz, preferably 5 Hz to 125 Hz, more preferably 5 Hz to 45 Hz, more preferably 25 Hz to 85 Hz, and more preferably 10 Hz to 30 Hz. When the preset modulating frequency is substantially the same as or approximate to the operational neuronal firing frequency at the brain functional site, the brain functional site can be modulated to operate properly at the operational neuronal firing frequency, to treat or prevent diseases at the brain functional site as well as to enhance brain functions.

The method may be used for treatment and prevention of one or more of insomnia, Alzheimer's disease, epilepsy, and depression, or for facilitation of the brain in learning and memorizing. In addition, the method may be further used for treatment and prevention of other diseases of the brain, by properly adjusting the wavelength $\lambda$ of the generated electromagnetic field based on the dimension of the brain functional site and properly designating the preset modulating frequency based on the operational neuronal firing frequency at the brain functional site.

In an instance, when the brain functional site is a brain sleep promoting site, the method may further comprise:

transforming the brain from its wake mode to its sleep mode by modulating the brain sleep promoting site at the preset modulating frequency with the power provided by the near field to have the brain itself remove the waste generated by the neurons in the wake mode of the brain, through the brain's glymphatic system that is working effectively only in the brain's sleep mode;

further transforming the brain to a rapid eye movement (REM) sleep stage by modulating the brain sleep promoting site at the preset modulating frequency with the power provided by the near field; and once the brain has reached the REM sleep stage in its sleep mode, modulating one or more other brain functional sites, especially the functional sites involved in learning and memory, with another modulating frequency different from the preset modulating frequency to facilitate the brain's natural process of having the neurons involved in consumption of proteins complete their consumption through about the same neuronal connecting networking environment as they were working during the wake mode in consuming the proteins.

In another aspect, there is provided an apparatus of modulating a neuronal firing frequency at a brain functional site in a brain, comprising a signal generation module and an antenna connected to the signal generation module, wherein the signal generation module is configured to generate an electrical signal with its power modulated with a preset modulating frequency in a burst format, and send the electrical signal to the antenna; and the antenna is configured to receive the modulated electrical signal from the signal generation module and generate an electromagnetic field with its power in variation at the preset modulating frequency based on the electrical signal;

wherein when the apparatus is placed near the brain so that the targeted brain functional site is within the range of the near field of the electromagnetic field, extracellular fluid at the brain functional site is polarized with the power of the electromagnetic field, such that a polarization density of the extracellular fluid varies at the preset modulating frequency and neurons in the extracellular fluid are modulated to fire at the preset modulating frequency.

The near field of the electromagnetic field satisfies the condition of $$0 < d \leq 0.62 * \sqrt{\frac{D^3}{\lambda}},$$

wherein d represents the distance from the antenna to an edge of the near field where the near field ends, D represents the largest dimension of the antenna, and λ represents the wavelength of the generated electromagnetic field in vacuum.

The wavelength λ of the generated electromagnetic field in vacuum is such that the wavelength of the electromagnetic field at the brain functional site matches the dimension of the brain functional site.

Additionally or alternatively, the wavelength λ of the generated electromagnetic field in vacuum is such that the wavelength of the electromagnetic field at the brain functional site is from 70% to 130% of the dimension of the brain functional site.

The preset modulating frequency is determined based on the operational (or normal) neuronal firing frequency at the brain functional site and is preferably in the range of 1 Hz to 2500 Hz, preferably 5 Hz to 125 Hz, more preferably 5 Hz to 45 Hz, more preferably 25 Hz to 85 Hz, and more preferably 10 Hz to 30 Hz.

In an instance, when the targeted brain functional site is a brain sleep promoting site, the apparatus may be used for:

transforming the brain from its wake mode to its sleep mode by modulating the brain sleep promoting site at the preset modulating frequency with the power provided by the near field to have the brain itself remove the waste generated by the neurons in the wake mode of the brain, through the brain's glymphatic system that is working effectively only in the brain's sleep mode;

further transforming the brain to a rapid eye movement (REM) sleep stage by modulating the brain sleep promoting site at a particular modulating frequency with the power provided by the near field; and once the brain has reached the REM sleep stage in its sleep mode, modulating one or more other brain functional sites, especially the functional sites involved in learning and memory, with another particular modulating frequency to facilitate the brain's natural process of having the neurons involved in consumption of proteins complete their consumption through about the same neuronal connecting networking environment as they were working during the wake mode in consuming the proteins.

As would be appreciated by those skilled in the art, the advantages achieved by the above method can also be achieved by the above apparatus.

BRIEF DESCRIPTION OF DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DEAILED DESCRIPTION OF THE INVENTION

Some embodiments of the present invention will be described hereinafter with reference to the accompanying drawings.

Figure 1:
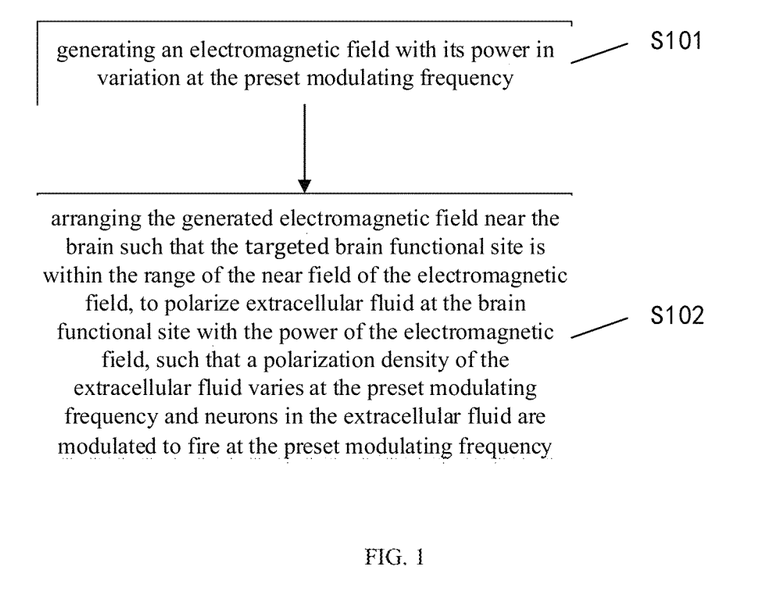
FIG. 1 is a schematic diagram showing a method of modulating a neuronal firing frequency at a brain functional site in a brain according to an embodiment of the present invention.

In an embodiment, as shown in FIG. 1, a method of modulating a neuronal firing frequency at a brain functional site in a brain includes:

Step S101 of generating an electromagnetic field with its power in variation at the preset modulating frequency; and Step S102 of arranging the generated electromagnetic field near the brain such that the targeted brain functional site is within the range of the near field of the electromagnetic field, to polarize extracellular fluid at the brain functional site with the power of the electromagnetic field, such that a polarization density of the extracellular fluid varies at the preset modulating frequency and neurons in the extracellular fluid are modulated to fire at the preset modulating frequency.

The near field of the electromagnetic field may be generated by an antenna and satisfy the condition of $$0 < d \le 0.62 * \sqrt{\frac{D^3}{\lambda}},$$

wherein d represents the distance from the antenna to an edge of the near field where the near field ends, D represents the largest dimension of the antenna, and λ represents the wavelength of the generated electromagnetic field in vacuum. Here, given that d satisfies the above condition, the electrical power from the antenna can be effectively transferred onto the targeted brain functional site within the near field through the inductive and capacitive effect of the current and charges in the antenna applied on the targeted brain functional site via the neuronal clusters formed by groups of neurons in the brain, which act as the secondary antennas for receiving the electrical power from the antenna to the targeted brain functional site within the near field.

As the brain is surrounded by the near field of the electromagnetic field generated by the antenna, through the strong inductive and capacitive effect of the currents and charges in the antenna, the neuronal clusters formed by groups of neurons in the brain act as the secondary antennas to receive the power from the antenna deep into the brain regions within the near field.

Here the near field is limited by the distance d from the antenna, the largest dimension D of the antenna, as well as the wavelength λ of the electromagnetic field generated by the antenna.

The wavelength λ of the generated electromagnetic field in vacuum is such that the wavelength of the generated electromagnetic field at the brain functional site matches the dimension of the brain functional site. In this way, the brain functional site can be efficiently modulated by the electromagnetic field.

Additionally or alternatively, the wavelength λ of the generated electromagnetic field in vacuum may be such that the wavelength of the electromagnetic field at the brain functional site is from 70% to 130% of the dimension of the brain functional site.

For example, in the case of selectively modulating the sleep promoting site ventrolateral preoptic nucleus (VLPO) in the brain, given that the dimension of the VLPO is about 1 cm and an electromagnetic field of 6 cm wavelength in vacuum will have a wavelength of 1 cm in the brain, the 1 cm wavelength matches the dimension of the VLPO for high modulation efficiency. In this case, the wavelength λ of the electromagnetic field is 6 cm and thus the frequency of the electromagnetic field is 5 GHz, and the largest dimension D of the antenna is 18 cm, then $$0 < d \le 0.62 * \sqrt{\frac{18^3}{6}} = 19.3 \text{ cm}$$

That is, the maximum distance of the near field is 19.3 cm from the antenna. Here, the value of the dimension D relates to the value of the distance d, and those skilled in the art knows proper adjustment of the values of D and d correlatively to properly acting the targeted brain functional site.

In the present embodiment, the electromagnetic field is generated through the antenna, where the antenna is placed near the brain such that the targeted functional site of the brain is within the near field of the generated electromagnetic field and the extracellular fluid in the object functional site is polarized by the electric field of the near field, and the power of the near field is modulated to appear in bursts with the preset modulating frequency such that the polarization density of the extracellular fluid in the object functional site varies at the same frequency as the variation frequency of the power (i.e. the preset modulating frequency), thereby modulating the neuronal firing frequency at the targeted brain functional site.

In an example of the above method, the brain is transformed from its wake mode to its sleep mode, in which an antenna generates an electromagnetic field with its near field acting on the brain for sleep induction. During operation, the antenna is located near the brain and the sleep promoting sites of the brain, including the ventrolateral preoptic nucleus (VLPO), is within the near field of the generated electromagnetic field and the extracellular fluid in the object functional site is polarized by the power of the near field, where the power of the electromagnetic field is modulated with a low frequency in a burst format such that the polarization density of the extracellular fluid in the object functional site varies at the same frequency as the variation frequency of the power, thereby modulating the neuronal firing frequency at the brain sleep promoting site (including modulating the VLPO to a certain frequency), inducing the brain to transform from the wake mode to the sleep mode. Herein, the frequency of the generated electromagnetic field is determined such that the wavelength of the generated electromagnetic field in the sleep-promoting site in the brain best matches the dimensions of the sleep-promoting site so that the modulating effect of the generated electromagnetic field is selective to the sleep-promoting site. The frequency of the generated electromagnetic field is in the range of 1 GHz to 20 GHz, preferably in the range of 4 GHz to 6 GHz. The modulating frequency for the variation of the power of the generated electromagnetic field is in the range of 5 Hz to 2500 Hz, preferably in the range of 10 Hz to 30 Hz.

In another example of the above method for the treatment and prevention of Alzheimer's disease, an antenna generates an electromagnetic field with its near field acting on the brain, to implement two sequential steps of: 1) transforming the brain from its wake mode to its sleep mode to have the brain itself remove the waste generated by the neurons in the wake mode of the brain, through the brain's glymphatic system that is working effectively only in the brain's sleep mode; 2) transforming the brain from its wake mode to its sleep mode up the rapid eye movement (REM) sleep stage by modulating the brain sleep promoting site at the preset modulating frequency with the power provided by the near field; and 3) once the brain has reached the REM sleep stage in its sleep mode, modulating one or more other brain functional sites, especially the functional sites involved in learning and memory, with another particular modulating frequency different from the preset modulating frequency to facilitate the brain's natural process of having the neurons involved in consumption of certain proteins, such as amyloid beta, complete their consumption through substantially the same neuronal connecting networking environment as they were working during the brain wake mode in consuming the proteins. During the operation, the antenna is located near the brain and all the functional sites of the brain, especially the brain functional sites for sleep promoting and for learning and memorizing, are within the near field of the generated electromagnetic field and the extracellular fluid in all the brain functional sites is polarized by the near field, and the power of the near field is modulated with the low preset modulating frequency in a burst format such that the polarization densities of the extracellular fluid in the brain functional sites vary at the same frequency as the variation frequency of the power of the electromagnetic field, thereby modulating the neuronal firing frequency at the brain functional sites to the preset modulating frequency to transform the brain from wake mode to sleep mode, and then modulating the neuronal firing frequency to another frequency to facilitate the brain in its natural process of dealing with the left over proteins during the brain in wakefulness, which are the causes of Alzheimer's disease. The frequency of the generated electromagnetic field is determined such that the wavelength of the generated electromagnetic field in the sleep-promoting site best matches the dimensions of the sleep-promoting site as well as the learning and memorizing sites in the brain so that the modulating effect of the generated electromagnetic field is selective to the sleep-promoting site as well as the learning and memorizing sites. The frequency of the electromagnetic field is in the range of 1 GHz to 20 GHz, preferably in the range of 4 GHz to 6 GHz. The modulating frequency for the variation of the power of the generated electromagnetic field is in the range of 5 Hz to 2500 Hz, preferably in the range of 10 Hz to 30 Hz.

In another example of the above method, an antenna generates an electromagnetic field having power varying at the preset modulating frequency, with its near field acting on the brain. During the operation, the antenna is located near the brain and the part of the brain that is epileptically diseased is within the near field of the generated electromagnetic field and the extracellular fluid in this part of the brain is polarized by the near field; the power of the near field is modulated with a low frequency (i.e. the preset modulating frequency) in a burst format to make the polarization densities of the extracellular fluid in the brain functional sites vary at the same frequency as the variation frequency of the power, thereby modulating the neurons at the epileptically diseased part of the brain to fire at the normal frequency when this part of the brain is not epileptically diseased, until the epileptically diseased neurons have been rehabilitated to normal in their firing and the epilepsy is cured. The frequency of the generated electromagnetic field is determined such that the wavelength of the generated electromagnetic field at the epileptically diseased part of the brain best matches the dimensions of the epileptically diseased part of the brain so that the modulating effect of the generated electromagnetic field is selective to the epileptically diseased part of the brain. The frequency of the electromagnetic field is in the range of 300 MHz to 20 GHz. The modulating frequency for the variation of the power of the generated electromagnetic field is in the range of 1 Hz to 2500 Hz with the optimum in the range of 5 Hz to 45 Hz.

In another example of the above method to modulate the brain for treatment of depression, a current signal with its amplitude modulated at a low frequency is transferred to an antenna to generate an electromagnetic field with its near field acting on the brain functional sites that are responsible for serotonin (i.e. diminished activity of serotonin pathways plays a causal role in the pathophysiology of depression) release in the brain, including the subcallosal cingulate gyms (SCG). During the operation, the antenna is located near the brain and the part of the brain that is responsible for serotonin release is within the near field of the generated electromagnetic field and the extracellular fluid in this part of the brain is polarized by the near field; the power of the near field is modulated with a low frequency in a burst format to make the polarization densities of the extracellular fluid in the brain functional sites vary at the same frequency as the variation frequency of the power, thereby modulating the neuronal firing frequency at the part of the brain to fire at the frequency they normally do when the brain is free of depression. In this way the neurons in the part of the brain are rehabilitated back to their normal firing behaviors and the depression in the brain is cured. Here, the frequency of the generated electromagnetic field is determined such that the wavelength of the generated electromagnetic field in the brain functional sites that are responsible for serotonin release in the brain best matches the dimensions of the brain functional sites, including the subcallosal cingulate gyrus (SCG) so that the modulating effect of the generated electromagnetic field is selective to these brain functional sites. The frequency of the electromagnetic frequency may be in the range of 1 GHz to 20 GHz. The modulating frequency for the variation of the power of the generated electromagnetic field is in the range of 1 Hz to 2500 Hz, preferably in the range of 5 Hz to 45 Hz.

In another example of the above method which is used to facilitate the brain in learning and memorizing, a current signal with its amplitude modulated at a low frequency is transferred to an antenna to generate an electromagnetic field with its near field acting on the brain functional sites that are responsible for learning and memorizing, including the frontal lobe and temporal lobe. During the operation, the antenna is placed near the concerned brain functional sites such that the brain functional sites are within the near field of the generated electromagnetic field and the extracellular fluid in this part of the brain is polarized by the near field; the power of the near field is modulated with a low frequency in a burst format to make the polarization densities of the extracellular fluid in the brain functional sites vary at the same frequency as the variation frequency of the power, thereby modulating all the neurons in the concerned brain functional sites to fire at a critical frequency for binding between the neurons via their synapses. With the modulation much more synapses of the neurons in the concerned brain functional sites are activated/alerted for binding such that the brain learns faster and memorizing more solidly. In the example, the frequency of the generated electromagnetic field is determined such that the wavelength of the generated electromagnetic field at the brain functional sites that are responsible for learning and memorizing best matches the dimensions of the brain functional sites so that the modulating effect of the generated electromagnetic field is selective to these brain functional sites. The frequency of the electromagnetic field is in the range of 300 MHz to 20 GHz, preferably in the range of 2 GHz to 10 GHz. The modulating frequency for the variation of the power of the generated electromagnetic field is in the range of 1 Hz to 2500 Hz, preferably in the range of 25 Hz to 85 Hz.

Likewise, the above method can be used for the treatment and prevention of insomnia.

As can be seen, the frequency (or the wavelength λ) of the generated electromagnetic field in vacuum is determined depending on the dimension of the targeted brain functional site, and the preset modulating frequency for modulating the power of the electromagnetic field is determined based on the operational neuronal firing frequency at the brain functional site and may be in the range of 1 Hz to 2500 Hz, preferably 5 Hz to 125 Hz, more preferably 5 Hz to 45 Hz, more preferably 25 Hz to 85 Hz, and more preferably 10 Hz to 30 Hz.

The method can be used for treatment and prevention of one or more of insomnia, Alzheimer's disease, epilepsy, and depression, or for facilitation of the brain in learning and memorizing.

In another embodiment, there is provided an apparatus of modulating a neuronal firing frequency at a brain functional site in a brain. Various examples of the apparatus are illustratively described below.

Figure 2:
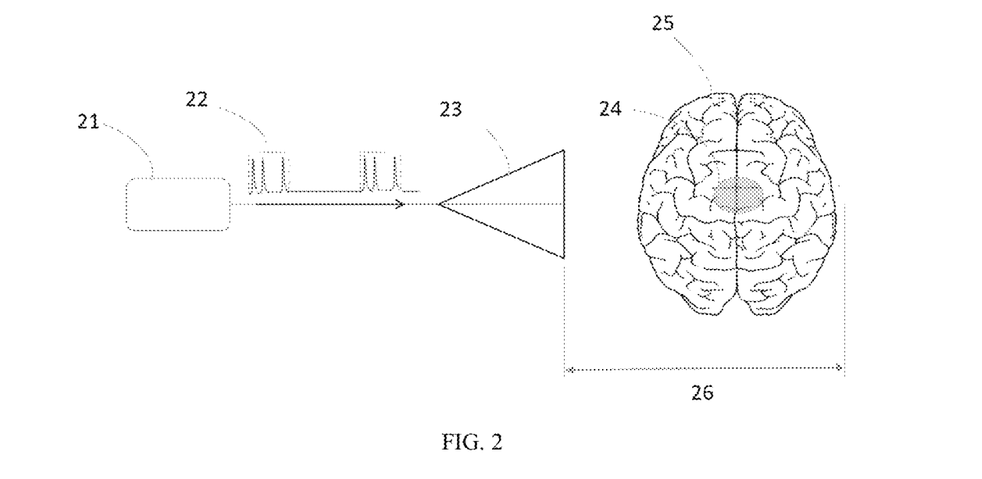
FIG. 2 schematically shows an apparatus of modulating a neuronal firing frequency at a brain functional site in a brain, in which a signal generation module generates and sends an electrical signal, e.g. a current signal with its amplitude modulated at a low frequency, to an antenna to generate an electromagnetic field with its near field acting on the brain to transform the brain from its wake mode to its sleep mode, according to an embodiment of the present invention.

As shown in FIG. 2, an apparatus of the present embodiment, which is for example used for sleep induction, includes a signal generation module 21 and an antenna 23 connected to the signal generation module 21. The signal generation module 21 is configured to generate a current signal with its amplitude modulated with a preset low modulating frequency in a burst format 22 and send the current signal to the antenna 23. Therefore, the antenna 23 receives the modulated electrical signal from the signal generation module 21 and generates an electromagnetic field with its near field range 26 covering the sleep promoting site 24 of the brain 25, polarizing the extracellular fluid in the sleep promoting site 24 and inducing a variation of the polarization density at the modulating frequency such that the neuronal firing frequency is modulated to the modulated frequency for transforming the brain 25 from wake to sleep. Here, the electromagnetic field has power varying at the preset modulating frequency.

Figure 3:
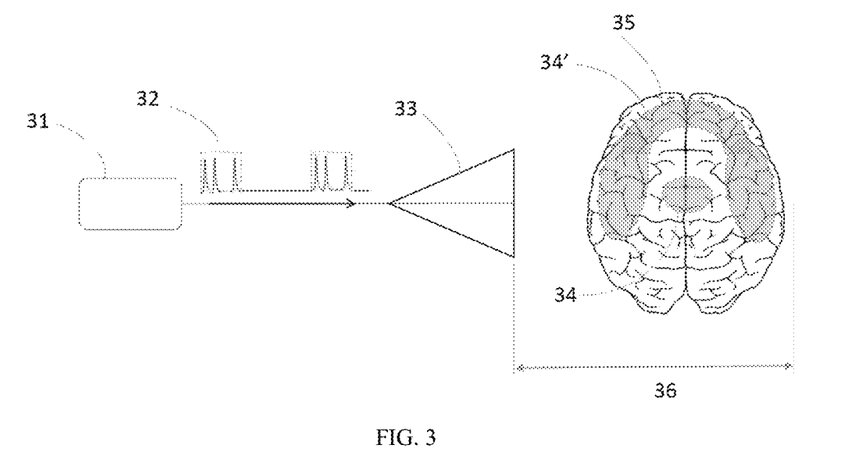
FIG. 3 schematically shows an apparatus of modulating a neuronal firing frequency at a brain functional site in a brain, in which a signal generation module generates and sends a series of electrical signals, e.g. current signals with its amplitude modulated at low frequencies, to an antenna to generate an electromagnetic field with its near field acting on the brain to facilitate the brain in its process of cleaning accumulated waste in the brain as well as completing the consumption of left over proteins surrounding the neurons for purposes of treatment and prevention of Alzheimer's disease, according to another embodiment of the present invention.

As shown in FIG. 3, an apparatus of the present embodiment, which is used for treatment and prevention of Alzheimer's disease, includes a signal generation module 31 and an antenna 33 connected to the signal generation module 31. The signal generation module 31 is configured to generate a current signal with its amplitude modulated with a preset low modulating frequency in a burst format 32 and send the current signal to the antenna 33. The antenna 33 receives the modulated electrical signal from the signal generation module 31 and generates an electromagnetic field with its near field range 36 covering the sleep promoting site 34 and the learning and memorizing sites 34' as well as other sites of the brain 35, thereby firstly polarizing the extracellular fluid in the brain functional sites and inducing variation of the polarization density at the brain functional sites with the preset modulating frequency such that the neuronal firing at the sleep promoting site 34 is modulated to transform the brain 35 from wake to sleep to facilitate the glymphatic system removal of waste generated by the neurons in the brain 35; and then, as the brain 35 is in its sleep mode, inducing the polarization density at the learning and memorizing sites 34' as well as other sites of the brain 35 to vary at another particular frequency such that the neuronal firing at the learning and memorizing sites 34' as well as other sites of the brain 35 is modulated to the another particular frequency that facilitates synaptic connections between the neurons in consumption/absorption of the leftover proteins from the wake mode of the brain 35; both of these facilitation processes provide the effect of treatment and prevention of Alzheimer's disease to the brain 35.

Figure 4:
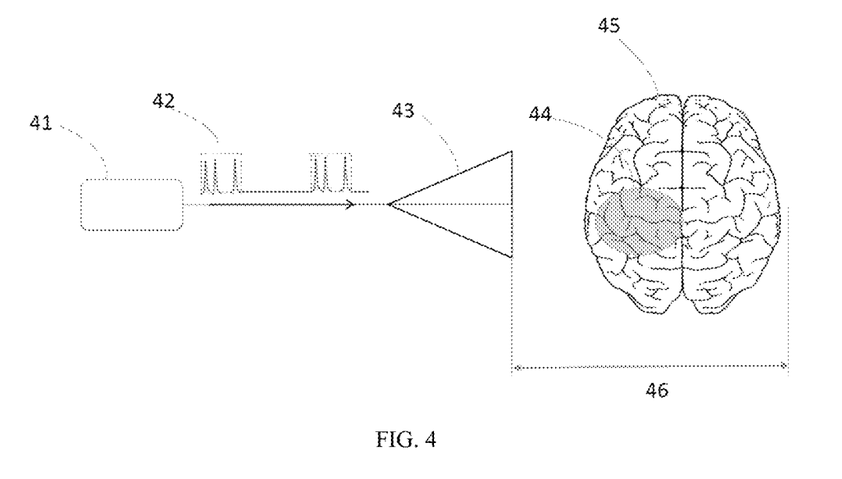
FIG. 4 schematically shows an apparatus of modulating a neuronal firing frequency at a brain functional site in a brain, in which a signal generation module generates and sends an electrical signal, e.g. a current signal with its amplitude modulated at a low frequency, to an antenna to generate an electromagnetic field with its near field acting on the brain to modulate the brain for treatment of epilepsy, according to another embodiment of the present invention.

As shown in FIG. 4, an apparatus of the present embodiment, which is used for treatment of epilepsy, includes a signal generation module 41 and an antenna 43 connected to the signal generation module 41. The signal generation module 41 is configured to generate a current signal with its amplitude modulated with a preset low modulating frequency in a burst format 42 and send the current signal to the antenna 43. The antenna 43 receives the modulated electrical signal from the signal generation module 41 and generates an electromagnetic field with its near field range 46 covering the epileptically diseased part 44 of the brain 45, thereby polarizing the extracellular fluid in the epileptically diseased part 44 of the brain 45 and inducing a variation of the polarization density at the modulating frequency that is the normal neuronal firing frequency for this part 44 of the brain 45 when it is not epileptically diseased to modulate the neurons in the epileptically diseased part 44 to fire at the modulating frequency such that the neurons are rehabilitated to normal in their neuronal firing behavior and the epilepsy in the brain 45 is cured.

Figure 5:
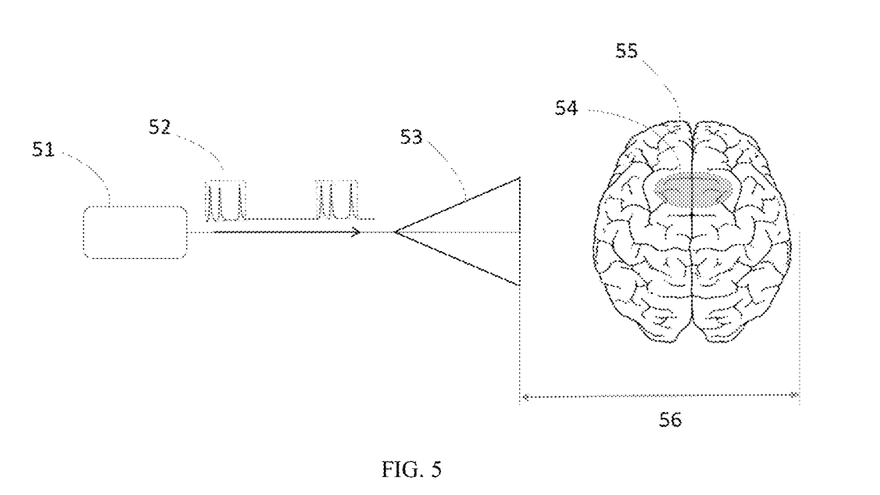
FIG. 5 schematically shows an apparatus of modulating a neuronal firing frequency at a brain functional site in a brain, in which a signal generation module generates and sends an electrical signal, e.g. a current signal with its amplitude modulated at a low frequency, to an antenna to generate an electromagnetic field with its near field acting on the brain functional sites that are responsible for serotonin release in the brain, including the SCG, to modulate the brain for treatment of depression, according to another embodiment of the present invention.

As shown in FIG. 5, an apparatus of the present embodiment, which is used for treatment of depression, includes a signal generation module 51 and an antenna 53 connected to the signal generation module 51. The signal generation module 51 is configured to generate a current signal with its amplitude modulated with a preset low modulating frequency in a burst format 52 and send the current signal to the antenna 53. The antenna 53 receives the modulated electrical signal from the signal generation module 51 and generates an electromagnetic field with its near field range 56 covering the brain functional sites that are responsible for serotonin release in the brain 55, including the SCG 54, thereby polarizing the extracellular fluid in the SCG 54 as well as the brain functional sites that are responsible for serotonin release in the brain 55, and inducing a variation of the polarization density at the modulating frequency that is the normal firing frequency of these brain functional sites when the brain 55 is free of depression, rehabilitating the neurons in these brain functional sites to their normal firing behaviors such that the depression in the brain 55 is cured.

Figure 6:
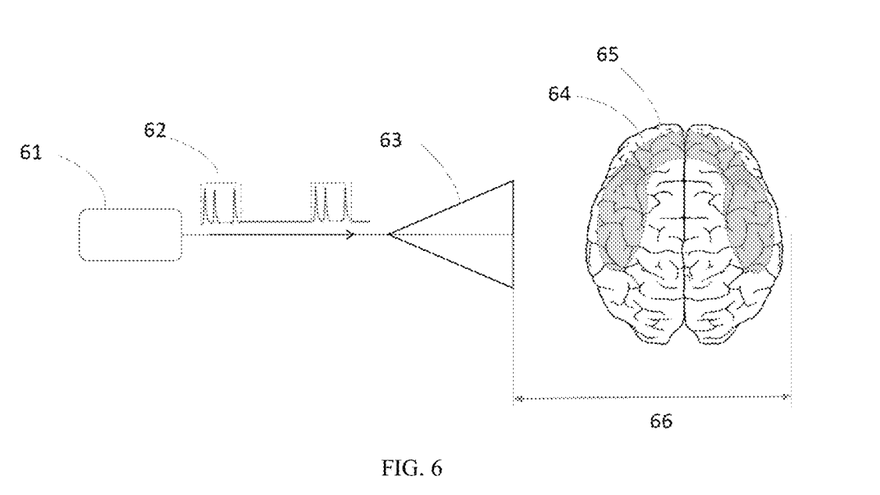
FIG. 6 schematically shows an apparatus of modulating a neuronal firing frequency at a brain functional site in a brain, in which a signal generation module generates and sends an electrical signal, e.g. a current signal with its amplitude modulated at a low frequency, to an antenna to generate an electromagnetic field with its near field acting on the brain functional sites that are responsible for learning and memorizing, including the frontal lobe and temporal lobe, to facilitate the brain in learning and memorizing, according to another embodiment of the present invention.

As shown in FIG. 6, an apparatus of the present embodiment, which is used for treatment of depression, includes a signal generation module 61 and an antenna 63 connected to the signal generation module 61. The signal generation module 61 is configured to generate a current signal with its amplitude modulated with a preset low modulating frequency in a burst format 62 and send the current signal to the antenna 63. The antenna 63 receives the modulated electrical signal from the signal generation module 61 and generates an electromagnetic field with its near field range 66 covering the learning and memorizing sites 64 as well as other brain functional sites in the brain 65, polarizing the extracellular fluid in the learning and memorizing sites 64 as well as other brain functional sites in the brain 65, and inducing a variation of the polarization density at a modulating frequency to modulate all the neurons in the concerned brain functional sites fire at a critical frequency for binding between the neurons via their synapses, activating much more than usual the synapses of the neurons in the concerned brain functional sites for binding such that the brain 65 learns faster and memorizing more solidly.

As to the apparatus in the above examples, the near field of the electromagnetic field satisfies the condition of $$0 < d \leq 0.62 * \sqrt{\frac{D^3}{\lambda}},$$

wherein d represents the distance from the antenna to an edge of the near field where the near field ends, D represents the largest dimension of the antenna, and λ represents the wavelength of the generated electromagnetic field in vacuum.

The wavelength λ of the generated electromagnetic field in vacuum is such that the wavelength of the electromagnetic field at the brain functional site matches the dimension of the brain functional site.

Additionally or alternatively, the wavelength λ of the generated electromagnetic field in vacuum is such that the wavelength of the electromagnetic field at the brain functional site is from 70% to 130% of the dimension of the brain functional site.

The preset modulating frequency is determined based on the operational (or normal) neuronal firing frequency at the brain functional site and is preferably in the range of 1 Hz to 2500 Hz, preferably 5 Hz to 125 Hz, more preferably 5 Hz to 45 Hz, more preferably 25 Hz to 85 Hz, and more preferably 10 Hz to 30 Hz.

In the above embodiments of the present invention, the waveform of the electromagnetic field generated by the antenna may be of any waveform, including but not limited to alternating waveform and pulse waveform.

While the invention is susceptible to various modifications and alternative forms, specific embodiments thereof have been shown by way of example in the drawings and the above detailed description. It should be understood, however, that it is not intended to limit the invention to the particular forms disclosed, but on the contrary, the intention is to cover all modifications, equivalents, and alternatives falling within the spirit and scope of the invention as defined by the appended claims.

It is expected that during the life of a patent maturing from this application many relevant disinfecting connectors will be developed; the scope of the term disinfecting connector is intended to include all such new technologies a priori.

The terms "comprises", "comprising", "includes", "including", "has", "having" and their conjugates mean "including but not limited to".

As used herein, the singular forms "a", "an" and "the" include plural references unless the context clearly dictates otherwise.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein and any number ranges based thereon are approximations within the accuracy of reasonable measurement and rounding errors as understood by persons skilled in the art.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

The invention claimed is:

1. A method of modulating a neuronal firing frequency at a brain sleep promoting site, the ventrolateral preoptic nucleus (VLPO), the method comprising:
generating an electromagnetic field having a power varying at a preset modulating frequency;
arranging the generated electromagnetic field near the brain such that the brain sleep promoting site is within a near field of the generated electromagnetic field;

modulating the brain sleep promoting site with the generated electromagnetic field at the preset modulating frequency, to polarize extracellular fluid at the brain sleep promoting site with the power of the electromagnetic field, such that a polarization density of the extracellular fluid varies at the preset modulating frequency and neurons in the extracellular fluid are modulated to fire at the preset modulating frequency to transition the brain from a wake mode to a sleep mode, wherein modulating the brain sleep promoting site facilitates the brain's glymphatic system removal of neuronal waste being the amyloid beta generated during the wake mode; and modulating the brain sleep promoting site with the generated electromagnetic field at the preset modulating frequency to further transition the brain to a rapid eye movement (REM) sleep stage, wherein the near field of the generated electromagnetic field is generated by an antenna and satisfies the condition of $$0 < d \leq 0.62 * \sqrt{\frac{D^3}{\lambda}},$$

wherein d represents a distance from the antenna to an edge of the near field where the near field ends, D represents a largest dimension of the antenna, and λ represents a wavelength of the generated electromagnetic field in vacuum.

2. The method of claim 1, wherein the wavelength λ of the generated electromagnetic field in vacuum is such that a wavelength of the generated electromagnetic field at the brain functional site matches a dimension of the brain functional site.

3. The method of claim 1, wherein the wavelength λ of the generated electromagnetic field in vacuum is such that a wavelength of the electromagnetic field at the brain functional site is from 70% to 130% of a dimension of the brain functional site.

4. The method of claim 1, wherein the preset modulating frequency is determined based on an operational neuronal firing frequency at the brain functional site and ranges from 1 Hz to 2500 Hz.

5. The method of claim 1, further comprising:
  modulating, once the brain transitions to the REM sleep stage, one or more of the frontal or temporal lobe with an electromagnetic field having a modulating frequency that is in a range of 25 Hz to 85 Hz and is different from the preset modulating frequency to facilitate neurons in the one or more of the front or temporal to consume a protein being the amyloid beta left over during the wake mode.

6. An apparatus for modulating a neuronal firing frequency at a brain sleep promoting site, the ventrolateral preoptic nucleus (VLPO), the apparatus comprising a signal generation module and an antenna connected to the signal generation module, wherein
  the signal generation module is configured to generate an electrical signal with its power modulated with a preset modulating frequency in a burst format, and send the electrical signal to the antenna;
  the antenna is configured to receive the modulated electrical signal from the signal generation module and generate an electromagnetic field having a power varying at the preset modulating frequency based on the electrical signal;
  wherein the apparatus is configured to perform following operations of:
  modulating, with the generated electromagnetic field at the preset modulating frequency, the brain sleep promoting site placed within a near field of the generated electromagnetic field, to polarize extracellular fluid at the brain sleep promoting site with the power of the electromagnetic field, such that a polarization density of the extracellular fluid varies at the preset modulating frequency and neurons in the extracellular fluid are modulated to fire at the preset modulating frequency, and to transition the brain from a wake mode to a sleep mode, wherein modulating the brain sleep promoting site facilitates the brain's glymphatic system removal of neuronal waste being the amyloid beta generated during the wake mode; and
  modulating the brain sleep promoting site with the generated electromagnetic field at the preset modulating frequency to further transition the brain to a rapid eye movement (REM) sleep stage,
  wherein the near field of the generated electromagnetic field satisfies the condition of $$0 < d \leq 0.62 * \sqrt{\frac{D^3}{\lambda}},$$

wherein d represents a distance from the antenna to an edge of the near field where the near field ends, D represents a largest dimension of the antenna, and λ represents the wavelength of the generated electromagnetic field in vacuum.

7. The apparatus of claim 6, wherein the wavelength λ of the generated electromagnetic field in vacuum is such that the wavelength of the electromagnetic field at the brain functional site matches the dimension of the brain functional site.

8. The apparatus of claim 6, wherein the preset modulating frequency is determined based on an operational neuronal firing frequency at the brain functional site and ranges from 1 Hz to 2500 Hz.

9. The apparatus of claim 6, wherein the apparatus is configured to further perform an operation of:
  modulating, once the brain transitions to the REM sleep stage, one or more of the frontal or temporal lobe with an electromagnetic field having a modulating frequency that is in a range of 25 Hz to 85 Hz and is different from the preset modulating frequency to facilitate neurons in the one or more of the frontal or temporal lobs to consume a protein being the amyloid beta left over during the wake mode.

* * * * *